United States Patent
Liebeskind et al.

(10) Patent No.: US 10,966,679 B2
(45) Date of Patent: Apr. 6, 2021

(54) PERFUSION DIGITAL SUBTRACTION ANGIOGRAPHY

(71) Applicant: THE REGENTS OF THE UNIVERSITY OF CALIFORNIA, Oakland, CA (US)

(72) Inventors: David S. Liebeskind, Los Angeles, CA (US); Fabien Scalzo, Tarzana, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 238 days.

(21) Appl. No.: 16/012,590

(22) Filed: Jun. 19, 2018

(65) Prior Publication Data

US 2019/0015061 A1    Jan. 17, 2019

Related U.S. Application Data

(63) Continuation of application No. PCT/US2016/067400, filed on Dec. 17, 2016.
(Continued)

(51) Int. Cl.
*A61B 6/00* (2006.01)
*G06T 7/00* (2017.01)

(52) U.S. Cl.
CPC .......... *A61B 6/5217* (2013.01); *A61B 6/461* (2013.01); *A61B 6/465* (2013.01); *A61B 6/481* (2013.01);
(Continued)

(58) Field of Classification Search
None
See application file for complete search history.

(56) References Cited

U.S. PATENT DOCUMENTS

| 7,945,082 | B2 | 5/2011 | Redel |
| 2005/0251010 | A1* | 11/2005 | Mistretta .............. A61B 6/507 600/407 |

(Continued)

FOREIGN PATENT DOCUMENTS

| JP | 2007536062 A | 12/2007 |
| JP | 2008525074 A | 7/2008 |

(Continued)

OTHER PUBLICATIONS

Patil et al (An improved model for describing the contrast bolus in perfusion MRI) (Year: 2011).*
(Continued)

*Primary Examiner* — Joel F Brutus
(74) *Attorney, Agent, or Firm* — O'Banion & Ritchey LLP; John P. O'Banion

(57) ABSTRACT

An apparatus and methodological framework are provided, named perfusion angiography, for the quantitative analysis and visualization of blood flow parameters from DSA images. The parameters, including cerebral blood flow (CBF) and cerebral blood volume (CBV), mean transit time (MTT), time-to-peak (TTP), and $T_{max}$, are computed using a bolus tracking method based on the deconvolution of time-density curves on a pixel-by-pixel basis. Individual contrast concentration curves of overlapping vessels can be delineated with multivariate Gamma fitting. The extracted parameters are each transformed into parametric maps of the target that can be color coded with different colors to represent parameter values within a particular set range. Side by side parametric maps with corresponding DSA images allow expert evaluation and condition diagnosis.

17 Claims, 8 Drawing Sheets

Related U.S. Application Data

(60) Provisional application No. 62/270,042, filed on Dec. 21, 2015.

(52) U.S. Cl.
CPC .............. *A61B 6/486* (2013.01); *A61B 6/487* (2013.01); *A61B 6/501* (2013.01); *A61B 6/504* (2013.01); *A61B 6/507* (2013.01); *A61B 6/5205* (2013.01); *G06T 7/0012* (2013.01); *G06T 2207/10124* (2013.01); *G06T 2207/20224* (2013.01); *G06T 2207/30016* (2013.01); *G06T 2207/30104* (2013.01)

(56) References Cited

U.S. PATENT DOCUMENTS

| | | | |
|---|---|---|---|
| 2008/0262344 A1* | 10/2008 | Brummett | A61B 5/0275 600/426 |
| 2009/0116711 A1 | 5/2009 | Larson | |
| 2010/0183116 A1* | 7/2010 | Zaiki | A61B 6/481 378/8 |
| 2010/0259550 A1 | 10/2010 | Baumgart | |
| 2010/0296714 A1* | 11/2010 | Schmainda | G01R 33/5601 382/131 |
| 2015/0173699 A1 | 6/2015 | Kyriakou | |
| 2015/0208930 A1 | 7/2015 | Gall | |
| 2015/0223744 A1 | 8/2015 | Bengi | |

FOREIGN PATENT DOCUMENTS

| | | |
|---|---|---|
| WO | 2005110231 A1 | 11/2005 |
| WO | 2006067201 A2 | 6/2006 |

OTHER PUBLICATIONS

Wang et al (Modified CT perfusion contrast injection protocols for improved CBF quantification with lower temporal sampling) (Year: 2008).*

European Patent Office (EPO), Supplementary European Search Report dated Aug. 13, 2019, related European patent application No. EP 16879915.3, pp. 1-10, claims searched, pp. 11-14.

Bogunovic, Hrvoje et al., "Estimating Perfusion Using X-ray Angiography", Proceedings of the 4th International Symposium on Image and Signal Processing and Analysis (2005), IEEE, Sep. 15, 2005, pp. 147-150.

Giordano, Marco et al., "Perfusion Estimation in the Peripheral Vasculature Using C-arm X-ray Systems", 2009 IEEE Nuclear Science Symposium and Medical Imaging Conference, Oct. 24, 2009, Conference Record, 2009, pp. 3017-3020.

Konstas, A. A., et al., "Theoretic Basis and Technical Implementations of CT Perfusion in Acute Ischemic Stroke, Part 1: Theoretic Basis", Physis Review, American Journal of Neuroradiology, vol. 30, No. 4, Mar. 6, 2009, pp. 662-668.

Korean Intellectual Property Office (KIPO), international search report and written opinion dated Mar. 29, 2017, related PCT international application No. PCT/US2016/067400, pp. 1-11, claims searched. pp. 12-16.

Japanese Patent Office (JPO), Office Action dated Dec. 1, 2020, related Japanese patent application No. JP 2018-532119, pp. 1-4, English-language translation, pp. 5-8, claims examined, pp. 6-13.

IP Australia, Examination report No. 1 for standard patent application dated Jan. 21, 2021, related Australian patent application No. 2016379175, pp. 1-4, claims examined, pp. 5-9.

* cited by examiner

```
10 ─┐
    ↘

20 ─┤ Acquire a sequence of digital subtraction
       angiography (DSA) images from an X-ray imager 30 ─┤ Calculate and plot tissue and arterial input function
       concentration time curves the DSA images 40 ─┤ Extract perfusion parameters from the DSA images
       and concentration time curves 50 ─┤ Generate parametric maps of extracted perfusion
       parameter data and DSA image data 60 ─┤ Display the perfusion angiography images
       on a visual display
```

FIG. 1

PERFUSION DIGITAL SUBTRACTION ANGIOGRAPHY

CROSS-REFERENCE TO RELATED APPLICATIONS

This application is a 35 U.S.C. § 111(a) continuation of PCT international application number PCT/US2016/067400 filed on Dec. 17, 2016, incorporated herein by reference in its entirety, which claims priority to, and the benefit of, U.S. provisional patent application Ser. No. 62/270,042 filed on Dec. 21, 2015, incorporated herein by reference in its entirety. Priority is claimed to each of the foregoing applications.

The above-referenced PCT international application was published as PCT International Publication No. WO 2017/112554 on Jun. 29, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND

1. Technical Field

The technology of this disclosure pertains generally to diagnostic imaging devices and methods, and more particularly to a system and methods for perfusion digital subtraction angiography for vessel blood flow visualization and quantitative analysis.

2. Background Discussion

Visualization of blood flow inside brain vessels is essential for the diagnosis and treatment evaluation of cerebrovascular disorders. Since its discovery, the application of X-ray for imaging purposes has greatly influenced medical diagnosis and interventions as it allows visualizing moving anatomical structures and endovascular devices. When directed towards the body and by passing through it, X-rays are partially absorbed and deflected, which causes attenuation of the incident beam. Various anatomical structures can be differentiated thanks to their specific level of absorption.

One of the decisive milestones of X-ray imaging was the introduction of angiography which has made the visualization of blood flow within vessels possible. The acquisition of an angiogram relies on X-ray imaging of iodinated radioopaque contrast agent previously injected into the blood stream. The blood flow is observed due to the high level of absorption of the contrast agent.

Over the years, the technique has improved and benefited from the appearance of digital cameras, leading to digital subtraction angiography (DSA), which allows for the unwanted elements such as bone and soft tissue to be removed by image subtraction from a set of successive images. Today, DSA remains a central and widely used imaging technique to assess blood flow during neurovascular interventions of stroke, for instance. In practice, several limitations hinder the use of DSA; images are qualitative; they are displayed in grayscale and need to be browsed frame by frame to observe temporal differences.

The popularity of DSA can be attributed to its good spatiotemporal resolution which is not easily matched by other acquisition techniques such as magnetic resonance imaging (MRI) and computed tomography (CT). Vascular abnormalities such as narrowing, blockage, or malformations can be visualized precisely in DSA. In addition, DSA is minimally invasive and is readily available in interventional suites of modern intensive care units (ICUs). Minimal cost, low risks, and rapid acquisition time are other features in favor of DSA. Although it may be argued that DSA will gradually be replaced in the future by CT angiography (CTA) during neurovascular interventions, DSA remains the gold standard worldwide.

Over the last three decades, numerous works have studied the role of DSA in both diagnosis and treatment evaluation of cardio- and cerebrovascular diseases. However, most of the existing studies were based on the visual review of image sequences by neurologists such that observations were collapsed to a simplified scale describing degree of reperfusion (Thrombolysis in Cerebral Infarction (TICI)) and recanalization (Arterial Occlusive Lesion (AOL)) after intervention.

These dichotomizations are still a matter of ongoing debate in the stroke community as their correlation with general outcome is limited and may also present interreader variability. There is a clear need to go beyond these manual scoring systems to obtain better evaluations for future clinical trials and endovascular devices. Although automatic TICI and AOL scores are still beyond the capabilities of current methods, automated algorithms for quantitative blood flow estimation have been developed over the last 20 years. They have failed so far to be translated into meaningful tools that could improve clinical practice and treatment evaluation.

The introduction of the image intensifier television (IITV) that converts the incident X-rays into a visible image was an ingredient to the success of angiography. With the modernization of computers in the 1980s, it became possible to record images digitally. This led to digital radiography which allows for more flexible visualization of digitally enhanced images. Digital subtraction angiography (DSA) extends digital radiography by subtracting a background image (obtained before injection of the contrast agent) from subsequent images. The purpose is to eliminate the bone and soft tissue images that would otherwise be superposed on the vessels. Despite excellent resolution characteristics, DSA has several inherent shortcomings.

First, DSA images are subjected to two major types of noise: the quantum noise due to the random nature of X-ray distribution and the noise resulting from the electronic components. In addition, the image subtraction operation amplifies the noise already present in images. To overcome this problem, noise reduction techniques need to be applied.

This leads to a second weakness of DSA: noise reduction algorithms are generally coded in the hardware and algorithms cannot easily be accessed or customized. Another limitation is the possible motion of the patient during the image acquisition that creates spatial blur and artifacts as the background image is not aligned to subsequent frames. Finally, visualization of the temporal information from DSA sequences is challenged by the fact that images are typically displayed in a video mode with raw grayscale frames. Only recently have commercial systems started to introduce color maps to better visualize the temporal information held in DSA.

Although DSA is technological evolution of digital radiography, DSA is associated with a computational layer that may also introduce significant inaccuracies in the presence of even minor patient motion. Because internal parameters and source images used by DSA are generally not made available by scanner manufacturers, further post-processing is particularly challenging. Despite these limiting factors, DSA remains the gold standard used during endovascular interventions.

Accordingly, there is a need for radiography imaging systems and methods that overcome these limitations and extend DSA by introducing a computational framework for the computation of perfusion angiography, for the quantitative analysis and visualization of perfusion and delay parameters from DSA.

BRIEF SUMMARY

The present technology provides a methodological framework for the quantitative analysis and visualization of blood flow parameters from DSA images. The parameters, including cerebral blood flow (CBF) and cerebral blood volume (CBV), mean transit time (MTT), time-to-peak (TTP), and $T_{max}$, can be reliably estimated using a bolus tracking method based on the deconvolution of the time density curve on a pixel-by-pixel basis. The imaging tool provides unique insights into flow mechanisms that cannot be observed directly in DSA sequences and may be used to quantify perfusion impact of endovascular interventions.

The post acquisition methods can provide imaging-based decision support to better guide and accelerate endovascular interventions in cases of acute stroke, for example. The neuroimaging methods can provide neurologists and neuro-interventionalists with an immense source of information for guidance in clinical decision making. Although the technology is illustrated with cerebral vascular imaging, the imaging system and methods can be adapted to image any part of the mammalian body.

Among available imaging techniques, DSA is a method of choice to visualize blood flow and to guide endovascular interventions. For example, biplane DSA provides high-resolution spatiotemporal images that have mostly been used qualitatively through the manual review of raw grayscale video. The interpretation of DSA images could benefit from color-coded perfusion parameters that would enable the visualization of hemodynamic features that are not directly visible on source angiograms and allow for refined decisions without any delay in care, added X-ray exposure, or higher dose of contrast agent.

The computational framework for the extraction of quantitative perfusion parameters from routine DSA uses a deconvolution technique to derive CBF, CBV, MTT, TTP, and $T_{max}$. A computational solution based on multimodal fitting is used to deal with overlap of the vessels. This demonstrates that routinely acquired DSA can be used to derive perfusion parameters that are similar in spirit to the ones obtained from CT/MR perfusion techniques. However, the interpretation of perfusion DSA is different due to the nature of the view (frontal or lateral) and the overlap of several brain structures within a given location.

A health practitioner may have several imaging modalities available for clinical evaluation of a patient including magnetic resonance imaging/angiography (MRI/MRA), diffusion/perfusion-weighted MRI, computed tomography/tomographic angiography (CT/CTA), perfusion CT, and digital subtraction angiography (DSA).

Broadly speaking, these images offer different insights and mirror different steps of the therapy. Neuroimaging may be used before treatment to classify the stroke using lesion size, tissue at risk, and involved vascular territory. This allows the identification of stroke patients who can benefit the most from a specific treatment strategy and outweigh its potential risks. DSA images are preferably acquired during therapy for decision-making. These iterative landmarks can be used to evaluate the degree of reperfusion and recanalization by visual scoring. Beyond the acute phase, neuroimaging is helpful in evaluating recovery and guiding other management strategies such as the augmentation of cerebral perfusion and reduction of mass effects from hemorrhage. Validation of perfusion angiography for estimation of hypoperfusion volume or degree of recanalization and reperfusion during endovascular interventions would be particularly helpful to health care providers.

The need for neuroimaging insight is triggered by the complexity of personalized treatment and the variability of stroke outcomes. The patient population in acute ischemic stroke settings is incredibly heterogeneous presenting a wide variety of outcomes and responses to treatment. For example, although the degree of recanalization correlates favorably with outcome, the risk of death remains stable. In addition, while the time from the onset of symptoms also correlates with outcome on average, it is not rare to observe that late recanalizers do better than early ones. These paradoxical observations can be linked to several factors such as blood pressure, NIH Stroke Scale (NIHSS), or age, but their individual predictive value is too weak for supporting prospective clinical decisions.

The presence of collateral circulation beyond the site of occlusion may also be decisive as it could sustain tissue viability until recanalization occurs; however, its presence largely varies across patients. Therefore, careful patient selection for endovascular intervention based on collateral circulation and tissue status is key to tailoring interventions and to improving patient outcomes. Currently, collateral flow can be evaluated on DSA but remains challenged by the lack of quantitative measurements.

According to one aspect of the technology, an image processing technique that allows for determination of contrast concentration time curves from biplane Digital Subtraction Angiograms (DSA) in the presence of vessel overlap. The estimated time curves can then be used to derive various perfusion parameters including Cerebral Blood Flow (CBF), Cerebral Blow Volume (CBV), and Mean Transit Time (MTT) from digital subtraction angiography (DSA).

According to another aspect of the technology, a system is provided for the estimation of contrast concentration time curves of individual, overlapped vessels from digital subtraction angiography (DSA) using parametric models.

Another aspect of the technology is to provide a Gamma mixture model that is estimated using expectation maximization.

A further aspect of the technology is to provide a system and method for vascular imaging that allows for the quantitative description of blood perfusion across the image that is integrated to the angiogram acquisition system to provide flow parameters within seconds to the clinician.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 1 is a schematic flow diagram of a method for the quantitative analysis and visualization of blood flow parameters from digital subtraction angiography (DSA) images according to one embodiment of the technology.

FIG. 4B is depicted by a circle and the diameter is increased proportionally with the number of patients observed with the same combination of values.

DETAILED DESCRIPTION

Figure 2A:
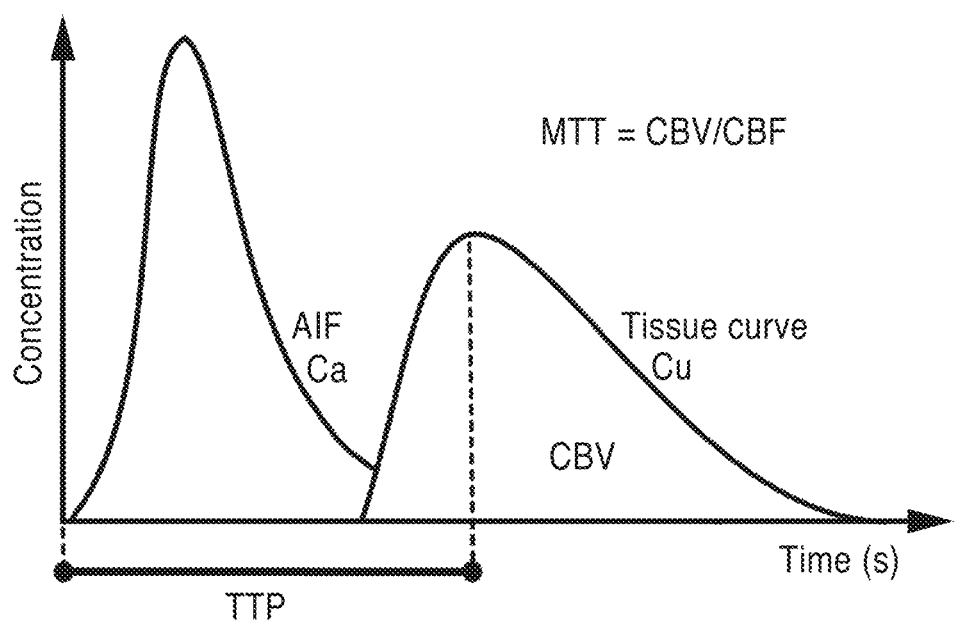
FIG. 2A is a tissue concentration time curve Cu with respect to an arterial input function (AIF) Ca. The deconvolution of the tissue curve Cu with Ca removes the dependence on the AIF and produces the residue function R. CBF is extracted at the maximum value reached at $T_{max}$ (FIG. 2B), while MTT is calculated as CBV/CBF, where CBV is determined as the area under the tissue curve (Cu).

Referring more specifically to the drawings, for illustrative purposes, embodiments of systems and methods for producing perfusion angiography images and quantitative analysis are generally shown. Several embodiments of the technology are described generally in FIG. 1 through FIG. 6F to illustrate the imaging system and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Turning now to FIG. 1, a flow diagram of one embodiment of a method 10 for performing perfusion angiography illustrated within the context of brain vasculature is generally shown. In the step at block 20 of FIG. 1, digital subtraction angiography of a subject is performed with an imager. Conventional DSA imaging systems are generally based on a radiation source, such as a fluoroscope and a detector that is integrated with a computer control, processor, display and storage. Preferred DSA systems have pulsed or continuous radiation sources with an X-Ray Image Intensifier and video detector and the initial images signals from the video detector are normally fed to the digital image processor of the computer for processing, manipulation, display and storage. The computer may also control an optical aperture that controls the illumination of the target so that it is set wide during patient and catheter positioning and narrowed during DSA fluoroscopic exposures and video detection.

Standard digital subtraction angiography (DSA) acquisition procedures involve the insertion of a catheter into an artery to a selected position. A radio-opaque contrast agent is then injected through the catheter and X-ray images are taken of the blood vessels over time. Typically, x-ray detection before and after the injection of the contrast agent produces 1 to 30 exposures a second that are delivered and processed by the computer software and stored.

The digitized image data that is obtained from the scanner makes it possible to "subtract" the pre-contrast images from later images obtained after the injection of the contrast agent. Two-dimensional perfusion images are automatically reconstructed with post-processing software on a computer processor or dedicated workstation. The acquired sequence of DSA image data from the scanner at block 20 can optionally be processed to eliminate artifacts related to patient motion or filtered, averaged or windowed to reduce noise etc.

The scanner data that is acquired at block 20 is then processed further to extract concentration time curves of the arterial input function at block 30 and to compute perfusion parameters from the DSA sequences and AIF at block 40 of FIG. 1. The extraction and computation of perfusion parameters is accomplished by post-processing software programming and no extra digital subtraction angiography (DSA) procedures have to be performed for this analysis.

Figure 2B:
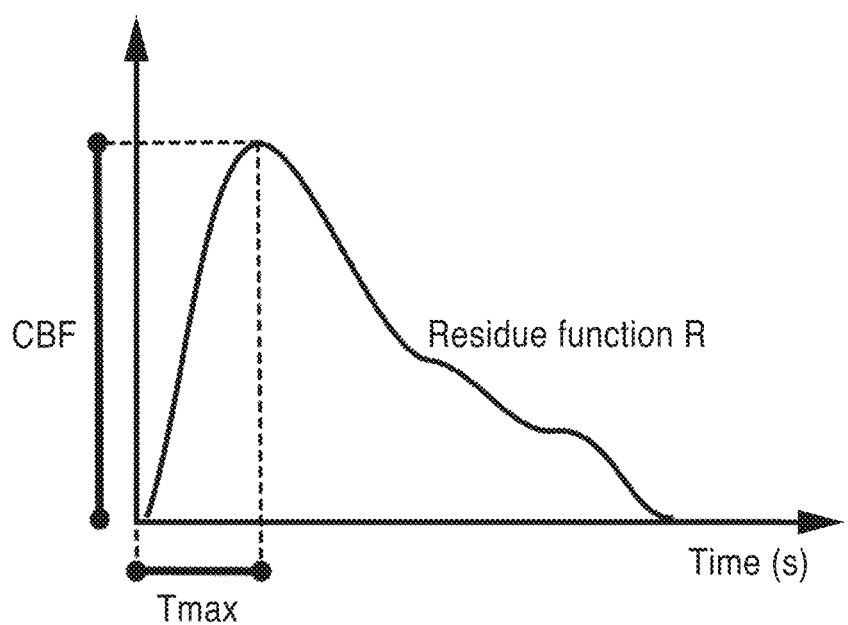
FIG. 2B is a graph of tissue concentration over time showing CBF and $T_{max}$. Because of the presence of arterial delays in stroke patients, the residue function is not always maximal at t=0, but might be maximal after a delay ($T_{max}$).

Tissue contrast concentration time curves ($C_u$) with respect to the arterial input function ($C_a$) from the DSA images are plotted at block 30 as illustrated in FIG. 2A and FIG. 2B. The concentration-time curve of the arterial input function ($C_a$) needed for the computation of perfusion maps is preferably obtained by extracting the average of the DSA values comprised within a region of interest (ROI) at each time point. The deconvolution of the tissue curve Cu with Ca removes the dependence on the AIF and produces the residue function R, which is used to derive the CBF and other parameters at block 40.

The extracted perfusion parameters produced at block 40 are mapped to make parametric maps at block 50 that are normally displayed sided by side with the corresponding DSA image at block 60. The maps are preferably color coded to represent parameter values above or below a threshold or within a range of values. The maps and images are then evaluated.

The video densitometric theory has established the relationship between the intensity of DSA images and blood flow. This theoretical foundation enables the computation of parametric maps summarizing blood volume, flow, and delay by tracking the injected contrast agent across the vasculature. The parameters, including cerebral blood flow (CBF) and cerebral blood volume (CBV), mean transit time (MTT), time-to-peak (TTP), and $T_{max}$, are computed using a bolus tracking method based on the deconvolution of the time-density curve on a pixel-by-pixel basis at block 30 and block 40.

To derive perfusion parameters from DSA sequences by bolus tracking analysis at block 40, the concentration C of the contrast agent at any location must be known. It can be estimated through DSA as the intensity observed in the image is proportional to the contrast concentration: $I(t)_{(x,y)} = k\mu C(t)_{(x,y)} \rho_{(x,y)}$, where $I(t)_{(x,y)}$ is the DSA image intensity value for a given pixel (x; y) at time t, $\mu$ is the mass attenuation coefficient of the contrast agent which is proportional to the x-ray energy, $\rho(x,y)$ is the thickness of the vessel lumen, C(x;y) is the contrast concentration, and k is a constant that accounts for the x-ray imaging system acquisition and amplification.

The vessel thickness (x,) can be computed using a framework that first applies a vessel detector based on vesselness filtering and thresholding. Centerlines are then obtained via skeletization.

Finally, a perpendicular segment (computed along each point of the centerline) is used to measure the distance to the edges of the vessel and derive the thickness assuming cylindrical volume. The thickness is then applied on a cross-sectional basis to every point within the vessel using bicubic interpolation.

With this information, it is possible to extract hemodynamic indices that will provide a quantitative description of the tissue status from DSA to quantify the degree of perfusion and delay at block 40 of FIG. 1. Bolus tracking algorithms are well established methods to determine flow and timing parameters of a bolus travelling from a source to a target location. From the contrast concentrations calculated above, it is possible to estimate the CBV at any location u in the image by calculating the amount of contrast agent $C_u$ that has passed through it with respect to the total amount of contrast measured at the feeding arterial vessel $C_a$ (i.e., arterial input function (AIF)):

$$CBV = \frac{\int_{t=0}^{\infty} C_u(t)dt}{\int_{t=0}^{\infty} C_a(t)dt}.$$

Assuming no recirculation and therefore unimodality of the contrast curves, it is common to use the peak of the contrast curve as a temporal landmark. The time taken to reach that maximum is called time-to-peak (TTP).

It can be shown that the temporal relationship between the concentration at the feeding artery $C_a$ and the target tissue $C_u$ can be written as:

$$C_u(t) = CBF(C_a(T) \otimes h(t),$$

where $\otimes$ is the symbol for the convolution and h is the distribution of the transit times, as the contrast agent follows different paths through the vasculature. The transit times are related to the fraction of injected contrast agent that is still present in the vasculature at any given time t. This measure is described by the residue function (t):

$$R(t) = 1 - \int_{\tau=0}^{t} h(\tau) d\tau.$$

From R, the relation between the concentrations $C_u$ and $C_a$ can be established as: $C_u(t) = CBF(C_a \otimes R)(t)$, which indicates that the contrast concentration $C_u(t)$ in the target tissue at a given time t is proportional to the amount of blood passing through per unit time (i.e., the CBF).

While the concentrations $C_u$ and $C_a$ can be estimated by DSA, the residual function R and CBF require more complex computations. In practice, the concentration curves $C_u$ and $C_a$ are sampled at discrete time points, $t_j \in [0, N-1]$:

$$C_u(t_j) = \Delta t CBF \sum_{i=0}^{N-1} C_a(t_i) R(t_j - t_i),$$

which can be rewritten in matrix-vector notation:

$$C_u = \Delta t CBF C_a R,$$

where $C_u, R \in \mathfrak{R}^N$ and $C_a$ is expanded to a Toeplitz matrix:

$$C_a = \begin{vmatrix} C_a(t_0) & 0 & \ldots & 0 \\ C_a(t_1) & C_a(t_0) & \ldots & 0 \\ \vdots & \vdots & \ddots & \vdots \\ C_a(t_{n-1}) & C_a(t_{n-2}) & \ldots & C_a(t_0) \end{vmatrix}$$

One way to recover R is to use singular value decomposition (SVD) of CA into two orthogonal matrices, U and $V^T$, and a diagonal matrix, W, with singular values ordered descendingly in the diagonal, $C_A = UWV^T$. The solution is then given by:

$$R = V\hat{W}^{-1} U^T C_u,$$

where the elements of $\hat{W}$ that are below the threshold are set to zero.

Given that max (R)=1, CBF is derived as the maximum of the estimated R, and Tmax is the time to reach this maximum. Once CBF has been estimated, MTT can be derived from the central volume theorem, MTT=CBV/CBF.

The list of parameters extracted (CBF, CBV, MTT, TTP, and $T_{max}$) are illustrated in the graphs of FIG. 2A and FIG. 2B. A tissue concentration-time curve $C_u$ with respect to an arterial input function (AIF) is indicated as ($C_a$) in FIG. 2A. The deconvolution of the tissue curve $C_u$ with $C_a$ removes the dependence on the AIF and produces the residue function R. CBF is extracted at the maximum value reached at $T_{max}$, while MTT is calculated as CBV/CBF, where CBV is determined as the area under the tissue curve ($C_u$). Because of the presence of arterial delays in stroke patients, the residue function is not always maximal at t=0 but might be maximal after a delay ($T_{max}$) as shown in FIG. 2B.

Figure 3A:
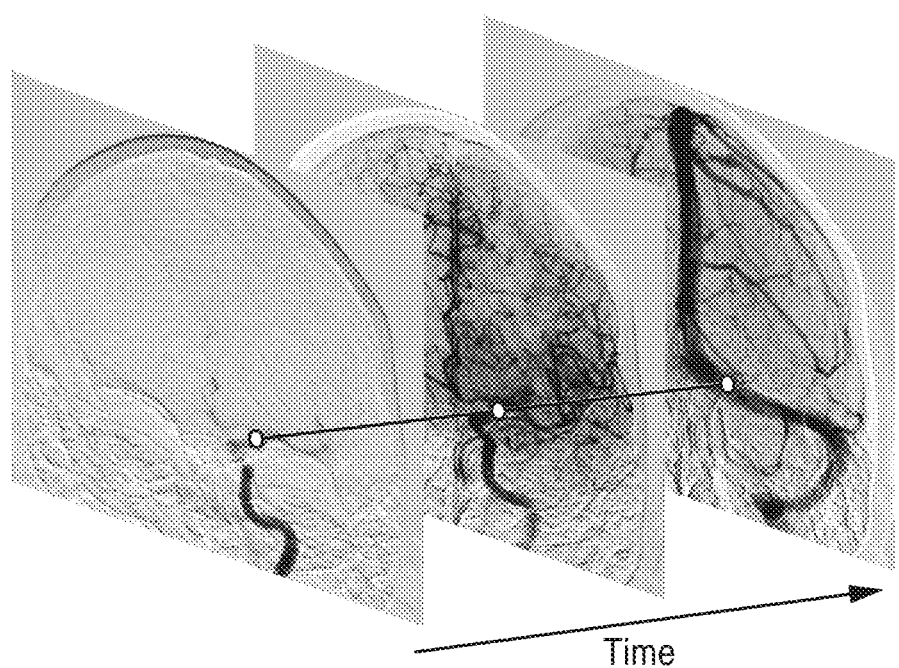
FIG. 3A is a temporal sequence of DSA images illustrating an overlap of vessels.
Figure 3B:
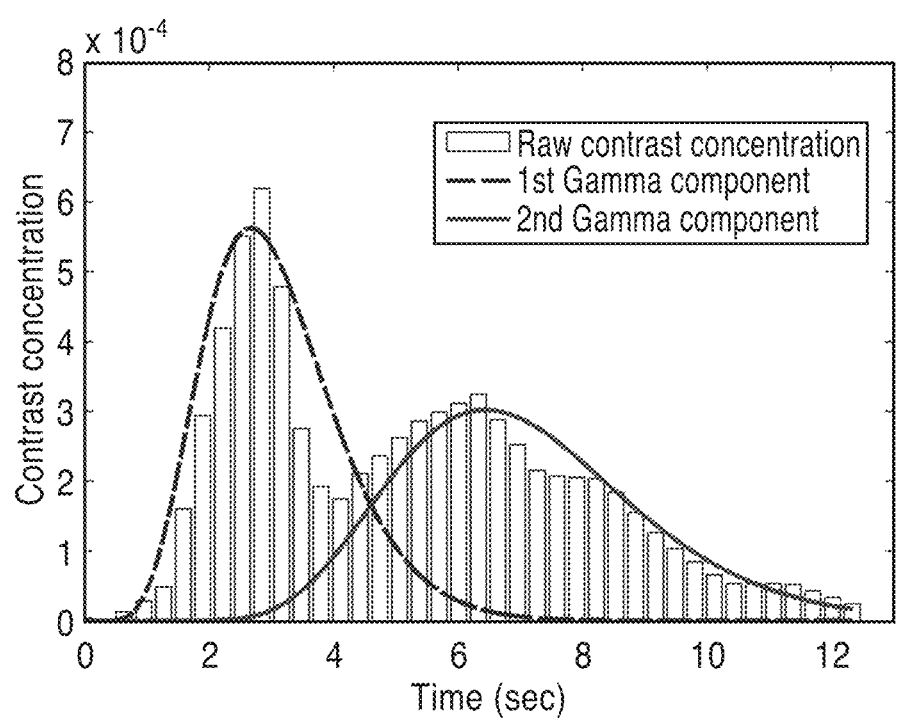
FIG. 3B is a bar graph bar graph of the contrast concentration-time curve of FIG. 3B is shown for a specific location in a DSA image sequence shown by open circles in FIG. 3A. The two contrast passages observed in the concentration-time curve are due to the overlap of the vessels. By applying the method based on the EM algorithm, it is possible to retrieve the individual components (represented by solid and dashed curves) of FIG. 3B using a Gamma mixture representation.

As illustrated in the sequence of frames shown in FIG. 3A, overlap of the vessels may occur in biplane DSA imaging and is one of the most challenging aspects of the estimation of perfusion parameters. One approach to solving the vessel overlap is the use of a Gamma mixture. This issue is illustrated in FIG. 3A and FIG. 3B where a selected image location in the image sequence, shown by open circles in FIG. 3A, presents two contrast passages that lead to two peaks in the concentration-time curve shown in FIG. 3B. The two contrast passages observed in the concentration-time curve are due to the overlap of the vessels. These two distributions correspond to the arterial and venous phase, respectively.

The deconvolution method presented above assumes unimodality of the concentration-time curve. Although it might be possible to use a previously acquired 3D model of the cerebrovasculature to delineate the vessels from the 2D projection, the capability of direct processing of biplane DSA without any prior imaging is of great interest since other imaging modalities are not always available. To solve this problem, the concentration is represented over time by a mixture of Gamma distributions that is automatically recovered at each point of the image using an expectation-maximization (EM) algorithm.

The Gamma-variate function is the most commonly used prior distribution to represent concentration-time curves as it has been shown to closely approximate the true contrast concentration. The estimation of the concentration-time curves is constrained by assuming a minimum transit time $\Delta_{min}$ between the injection site and the brain which ensures that the maximum of the fitted distribution (which is also its inflection point) lies within the restricted domain.

The density function $\gamma_{\alpha,\beta}$ is written as:

$$\gamma_{\alpha,\beta}(x) = \begin{cases} \frac{\beta^\alpha}{\Gamma(\alpha)} \exp^{-(x-\mu)\beta}(x-\mu)^{\alpha-1} & , \text{if } x-\mu \geq \Delta_{min}. \\ 0 \end{cases}$$

Otherwise, where $\alpha, \beta$ and $\mu$ are the shape, scale and location parameters, the Gamma function $\Gamma(\alpha)$ is written as:

$$\Gamma(\alpha) = \int_0^\infty t^{\alpha-1} \exp^{-t} dt.$$

The mean of the Gamma distribution is $\alpha/\beta$. The shape of the Gamma distribution is determined by the $\alpha$ parameter, which intuitively relates to the contrast concentration variation. When $\alpha > 1$, the distribution is bell-shaped, suggesting low heterogeneity. In the case of $\alpha < 1$, the distribution is highly skewed which indicates high variation. This flexibility makes the distribution suitable for accommodating with different concentration-time curves as observed at different locations in the image.

To capture multiple contrast passages at a given image location, the concentration curve over time is represented as a mixture of Gamma-variate distributions. This assumes that the overall distribution is generated from a few Gamma components, each with its own $\alpha$ and $\beta$ parameters. In the case illustrated in FIG. 3A, each component can be thought of as one contrast passage through one of the overlapped vessels at the current image location.

Where K represents the number of Gamma components in the mixture, and, the parameters of the jth component are denoted by $\alpha_j$ and $\beta_j$ and associated with the prior probability $\tau_j$, that a measured concentration was drawn from the current component, then the parameters of the overall distribution can be summarized as $\Theta = \{\alpha_j, \beta_j, \tau_j\}$, $j=1, \ldots$, with $$\sum_{j=1}^K \tau_j = 1.$$

The mixture is written as:

$$M(x, \Theta) = \sum_{j=1}^K \tau_j \gamma_{\alpha_j, \beta_j}(x),$$

where $\gamma_{\alpha_j, \beta_j}(x)$ is the Gamma-variate distribution of the jth component.

Optimization of the parameters $\Theta$ of the mixture is preferably posed as a maximum likelihood estimation (MLE). Here, the log-likelihood of parameter set $\Theta$ is obtained by approximation using a weighted sum over discrete time:

$$L(\Theta) = \sum_{i=1}^N \log M(x_i, \Theta),$$

where i represents a discrete time point.

The parameters $\Theta$ of the model are unknown and are estimated using an expectation-maximization (EM) algorithm which provides a convenient approximation in terms of an iterative maximization problem. To be able to estimate the parameter set $\Theta$ that maximizes L, the EM algorithm introduces an unobservable matrix $z \in \{0,1\}^{N \times K}$ to specify which Gamma component the ith observation $x_i$ comes from.

A soft EM definition is used where z is continuous and can take any value between 0 and 1 such that $z \in \{0,1\}^{N \times K}$, and where the sum of the weights of each observed data point i is equal to 1, $\sum_{j=1}^K z_{i,j} = 1$.

The complete discrete log-likelihood becomes:

$$L(\Theta) = \sum_{i=1}^N \sum_{j=1}^K z_{i,j} \log \tau_j + C,$$

$$C = \sum_{i=1}^N \sum_{j=1}^K z_{i,j} \log \gamma_{\alpha_j, \beta_j}(x_i).$$

The soft EM uses the log-likelihood and iterates between an E-step and an M-step. The E-Step comprises the calculation of the expected value $Q(\Theta, \Theta^m)$ of the log-likelihood given current parameters $\Theta^m$, and $$Q(\Theta, \Theta^m) = \sum_{i=1}^N \sum_{j=1}^K z_{i,j} \log \tau_j + C,$$

where $$z_{ij}^m = \frac{\tau_j^m \gamma_j(x_i; \alpha_j^m, \beta_j^m)}{M(x_i, \Theta^m)}.$$

The M-Step maximizes $Q(\Theta, \Theta^m)$ with respect to $\Theta$ using numerical optimization:

$$\Theta^{m+1} = \underset{\Theta}{\arg\max} Q(\Theta, \Theta^m).$$

The iterative procedure is executed until the convergence criterion $|\Theta^{m+1}-\Theta^m|<t_{em}$ is satisfied or the maximum number of iterations is reached (100). To avoid local maxima, it is repeated 5 times. The EM procedure can be performed for a different number of components $K \in [1,4]$, for instance. The number K can be selected so that it minimizes a Bayesian Information Criterion (BIC). To allow for faster convergence and reduce the risk of falling into local maxima, the procedure is initialized with a k-means algorithm.

Referring back to FIG. 1, at block 50 the acquired DSA images are transformed into perfusion angiography images that include parametric maps created with the calculated and extracted parameters once the parameters are obtained at block 30 and block 40. The parametric maps that are generated at block 50 for each selected parameter and overlaid or associated with the DSA images can be displayed at block 60 of FIG. 1.

For display purposes at block 60, each parametric map that is created at block 50 may be normalized and color-coded to facilitate visualization. The parametric maps can use any desired color coding scheme that is selected for pre-determined parameter levels.

For example, the color red could be selected to show high values, the color green for intermediate values and blue could be used to represent low values. Alternatively, the color coding of the map can have a color that represents a particular parameter that is above or below a set level or a color that represents a range of values. Multiple parameter maps of different parameters may be combined together and associated with the DSA image to show several parameters simultaneously in one embodiment.

In another embodiment, the DSA image-parametric map combinations are presented side by side at block 60. When reviewed as a composite or side-by-side, the CBF, CBV, and TTP maps can help the expert eye to differentiate between antegrade and collateral flow, identify risk of hemorrhage, perfusion deficits, delay, and flow stagnation, etc.

The technology described herein may be better understood with reference to the accompanying examples, which are intended for purposes of illustration only and should not be construed as in any sense limiting the scope of the technology described herein as defined in the claims Appended Hereto.

Example 1

To demonstrate the operational principles of the perfusion angiography framework and parametric imaging methods, data was collected from patients evaluated at a single, academic comprehensive stroke center and identified with symptoms of acute ischemic stroke. A total of 66 patients (median age: 68 years, including 35 women, satisfied the study criteria.

Source DSA images of each patient were processed with the perfusion angiography framework described in FIG. 1. The concentration time-curve of the arterial input function (AIF) (Ca) required for the computation of perfusion maps was obtained by extracting the average of the DSA values comprised within a region of interest (ROI) at each time point that was arbitrarily selected. In this illustration, the ROI was set on the intracerebral artery (ICA) as an elliptical region fully included in the vessel.

The capability of the method of extracting and calculating various parameters from the raw source DSA images and the estimation of the overlapped contrast concentration curves using Gamma fitting were tested. Similar to perfusion MRI, it was possible to detect or estimate the AIF automatically using constraints on early arrival time and maximum contrast values. However, to minimize possible source of error for the computation of perfusion parameters, the AIF was delineated manually. The parameters After processing, the following parameter maps were available; CBF, CBVfull, CBV, MTT, TTP, $T_{max}$, where CBVfull is the cerebral blood flow computed over the entire cerebral cycle (including arterial and venous phases) and CBV is computed during the arterial phase only.

The capability of the Gamma fitting method to delineate individual contrast concentration curves in the presence of overlap and noise was also evaluated and compared to a state-of-the-art fitting algorithm (RANSAC).

To verify the estimation of the overlapped contrast concentration curves and identification of the individual components using the multivariate Gamma fitting technique, the average AIF concentration curves were computed from 5 randomly selected patients from the dataset on which were selected a region of interest at a similar location on the intracerebral artery (ICA).

The average concentration curve was smoothed using a Gaussian filter and interpolated to produce a set of N=100 values using bicubic interpolation. The overlap was simulated by duplicating the contrast curve to create a vector, shifting the duplicated vector, and merging them into a single vector, thus creating a simulated overlap between two similar contrast curves. A set of merged concentration curves was created by varying the shifting amount from 5 to 100, ranging from almost full to no overlap. The objective was to then measure how accurately the processing scheme can fit and retrieve the two original contrast curves and using a Gamma-variate mixture from the merged contrast curve. In addition to the evaluation of the robustness to the amount of overlap, various levels of white Gaussian noise were added to the signal, ranging from a SNR of 500 to 5.

It was observed that the Gamma-variate fitting framework is able to accurately retrieve the two components of the mixture in the presence of noise when the overlap is below 55%. When the overlap is greater than 55%, the accuracy decreases significantly as the noise increases. As expected, the model had difficulty accurately recovering the two components in the presence of very high levels of noise (SNR<8) and high percentage of overlap (>70%).

Alternative methods to fitting Gamma distributions exist. For example, the least squares fitting scheme based on a discrete formulation would be possible but computationally costly. A more efficient technique is the random sample consensus (RANSAC) method that is typically used in computer vision to retrieve correspondence between images and estimate the geometric transformation matrix that relates them. The idea behind RANSAC is to estimate a large number of minimal-set fitting hypotheses. For each hypothesis, a robust score is calculated that is based on the alignment of the hypothesis with all points in the set. The best scoring minimal-set hypothesis is taken as the final estimate.

To compare functionality, a total of 300 fitting hypotheses were used and each hypothesis was made of 15 points. The accuracy of both the Gamma-variate and the RANSAC models was measured as the coefficient of determination or R-squared. For better estimation of the error, the process was repeated 10 times for each combination of error and overlap, and the average R-squared was reported.

Fitting results for four different combinations of overlap amount and noise levels were obtained. RANSAC recovers the components with a decent accuracy regardless of overlap until a SNR of about 10, and then the error drastically increases in the presence of higher levels of noise. In comparison, the standard estimation of TTP (without multimodal fitting) taken at the maximum of the concentration-time curve would be misplaced in half of the cases depending on which component is the highest.

Example 2

To further test the functionality of the methods, the perfusion angiography methods were applied to the dataset composed of DSA sequences following endovascular thrombectomy recorded on acute ischemic stroke patients with MCA occlusion. The tests are formulated such that the distribution of a given perfusion parameter across the MCA territory was averaged and studied with respect to the TICI score.

Statistical measurements of correlation and dispersion were then performed. Source DSA images of each patient were processed with perfusion angiography. The concentration-time curve of the arterial input function (AIF) Ca required for the computation of perfusion maps was obtained by extracting the average of the DSA values comprised within a region of interest (ROI) at each time point.

The perfusion angiography was conducted using the BIC criterion to select among a maximum of two Gamma components to differentiate between the arterial and the venous phase. After processing, the following parameter maps were available; CBF, $CBV_{full}$, CBV, MTT, TTP, and $T_{max}$, where $CBV_{full}$ is the cerebral blood flow computed over the entire cerebral cycle (including arterial and venous phases) and CBV is computed during the arterial phase only.

In order to evaluate the five perfusion parameters i.e. (CBF, $CBV_{full}$, CBV, MTT, TTP, $T_{max}$) the parameter maps needed to be transformed into a quantitative values $x_{map}$ that could be used as input to the statistical analysis. Each perfusion parameter was then characterized using the trimmed mean of the distribution of the values within the ROI. The trimmed mean computes the average of the values comprised between the 5th and 95th percentiles.

Pearson correlations were also evaluated between the following pairs of variables: (TICI, mRS), (NIHSS, mRS), (CBF, TICI), (CBV, TICI), (TTP, TICI), (MTT, TICI), ($T_{max}$, TICI), (CBF, mRS), (CBV, mRS), (TTP, mRS), (MTT, mRS), ($T_{max}$, mRS). To facilitate the statistical analysis, qualitative TICI scores ('0', '1', '2a', '2b', '3') are mapped to a continuous space, as follows: ('0', 0); ('1', 0.25); ('2a', 0.5); ('2b', 0.75); ('3', 1).

The perfusion angiography framework processed successfully 89% (59 out of 66) of the DSA images included in the dataset. Seven cases failed during processing due to either patient motion, short acquisition time (i.e., the DSA acquisition did not cover the entire injection cycle), poor image quality, or low temporal resolution (i.e., insufficient number of frames).

Figure 4A:
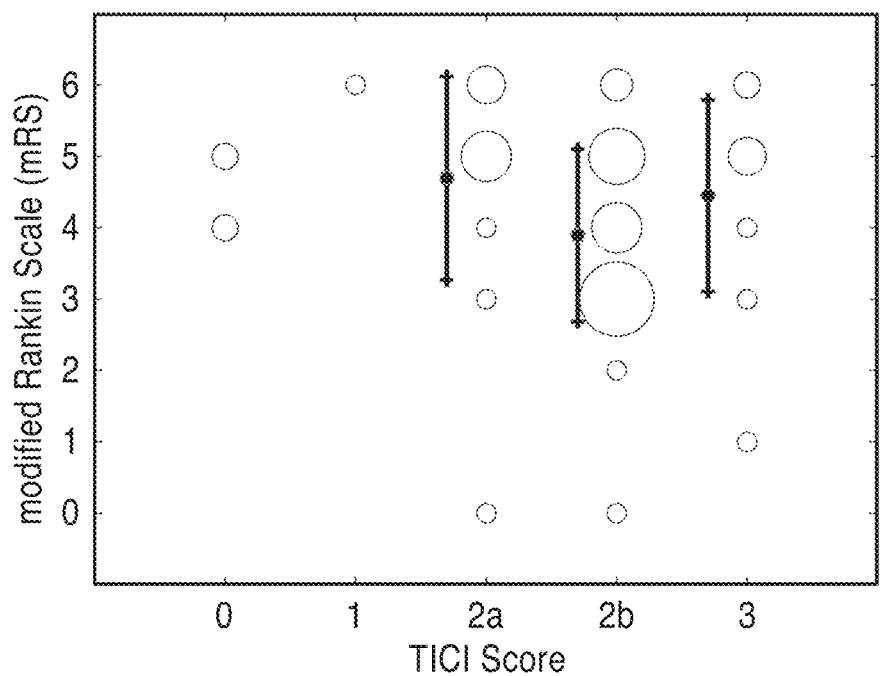
FIG. 4A is a scatter plot of the modified Rankin scale (mRS) outcome versus post endovascular intervention TICI score.
Figure 4B:
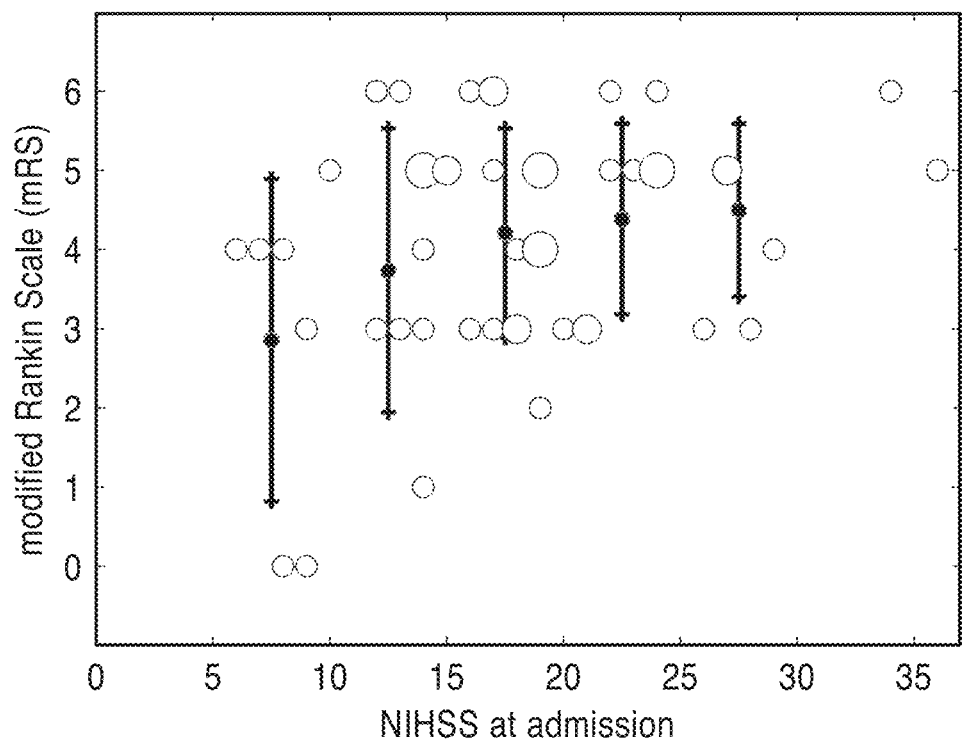
FIG. 4B is a scatter plot of the modified Rankin scale (mRS) outcome versus NIHSS at admission. Each patient in FIG. 4A

The overall distribution of outcomes in terms of modified Rankin Scale (mRS) is shown in FIG. 4A and FIG. 4B. On the graph of FIG. 4A, mRS is plotted with respect to TICI score assessed at the end of the endovascular intervention. On the graph of FIG. 4B, the plot illustrates the relationship between mRS and NIHSS at admission. Each patient is depicted by a circle; diameter is increased proportionally with the number of patients observed with the same combination of values.

It was noted that most of the patients included in the dataset (93%; 55 out of 59) had poor outcomes (mRS greater than or equal to 3). It was also observed that a TICI score of 2b leads to a slightly better mRS outcome than 2a. However, patients that reached a TICI score of 3 (i.e., complete reperfusion of the MCA territory) were not associated with a better outcome than 2b patients that may be attributable to the phenomenon of futile recanalization. One possible explanation may include an increased risk of hemorrhagic transformation.

As expected and shown in FIG. 4B, NIHSS at admission is linearly correlated with mRS outcome (r=0:304; p<0: 028). In addition, low NIHSS's (i.e. not severe) are associated with larger variations in terms of outcome.

Figure 5:
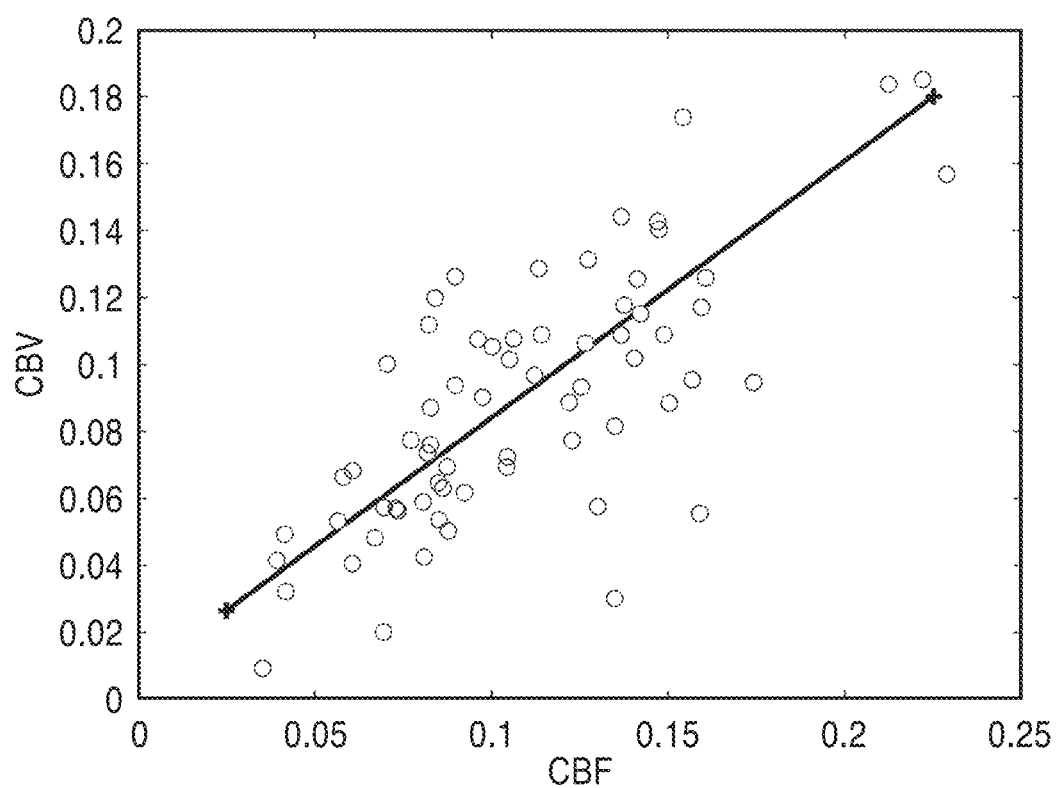
FIG. 5 is a scatter plot showing average CBV versus average CBF across the MCA territory in patients with acute stroke. Red line is obtained by linear regression and offers a very significant correlation (r=0:7361; $p<10^{-12}$).

Linear regression analysis between CBF and CBV values shown in FIG. 5 revealed an overall strong correlation (r=0.736, p<$10^{-12}$). Both values were estimated with perfusion angiography and averaged over the entire MCA territory. CBV was computed during the arterial phase of the cycle. This is an expected result that has been shown in previous MR and CT studies of perfusion and could in principle be used to identify infarcted areas from penumbra.

Figure 6A:
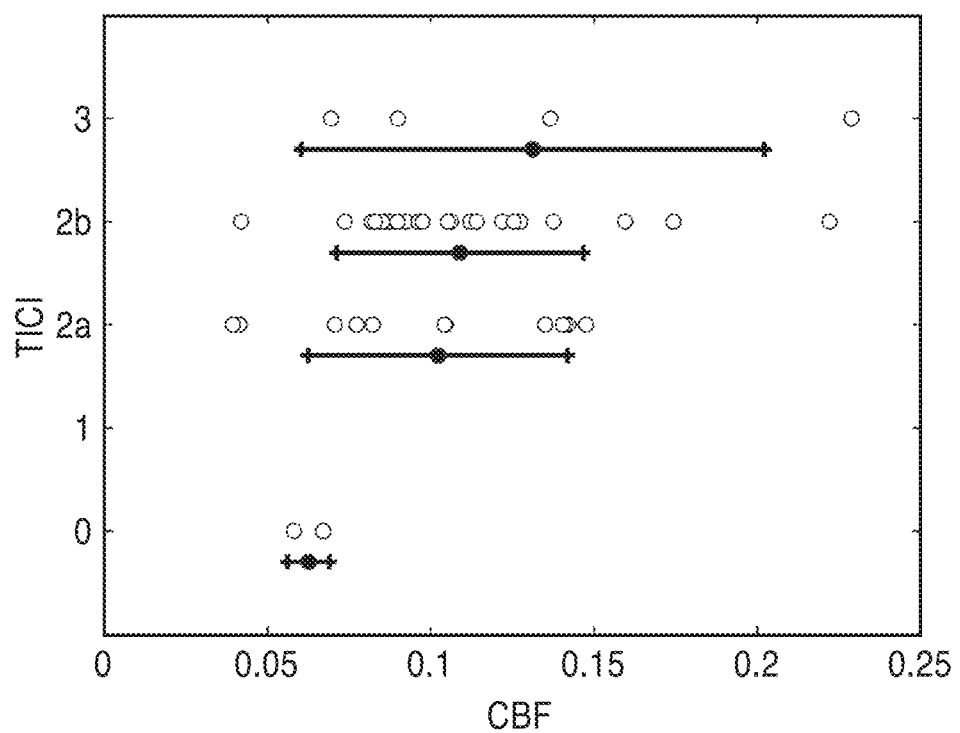
FIG. 6A is scatter plot representing the perfusion angiography parameter CBF versus TICI score. Average and standard deviation for specific TICI values are depicted by horizontal lines.
Figure 6B:
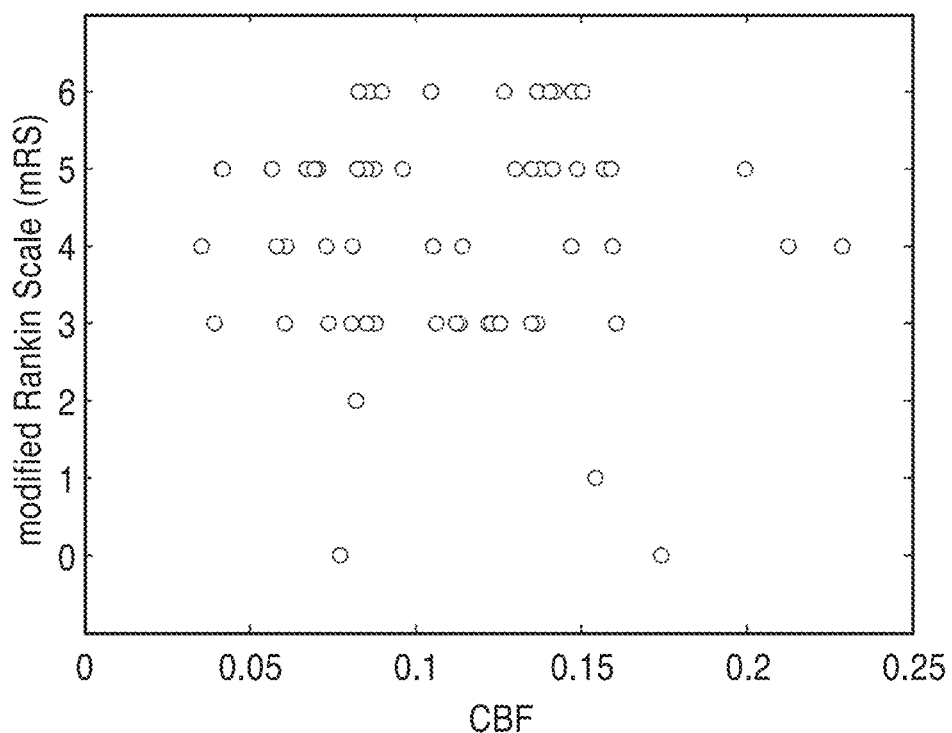
FIG. 6B is a scatter plot representing the perfusion angiography parameters CBF vs. mRS outcome.
Figure 6C:
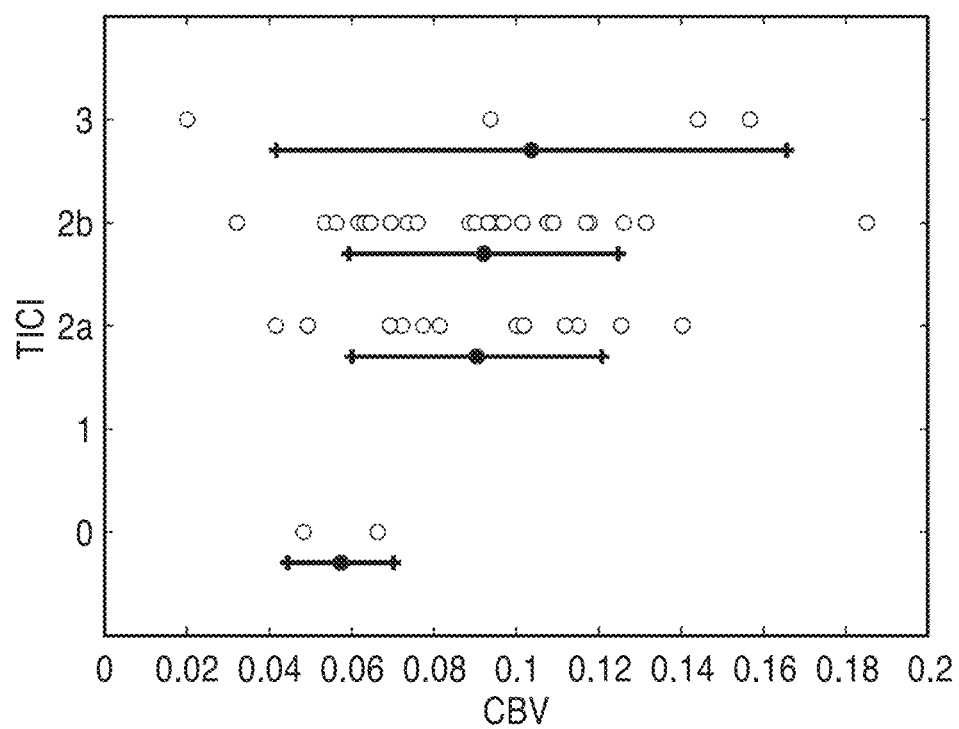
FIG. 6C is scatter plot representing the perfusion angiography parameter CBV versus TICI score. Average and standard deviation for specific TICI values are depicted by horizontal lines.
Figure 6D:
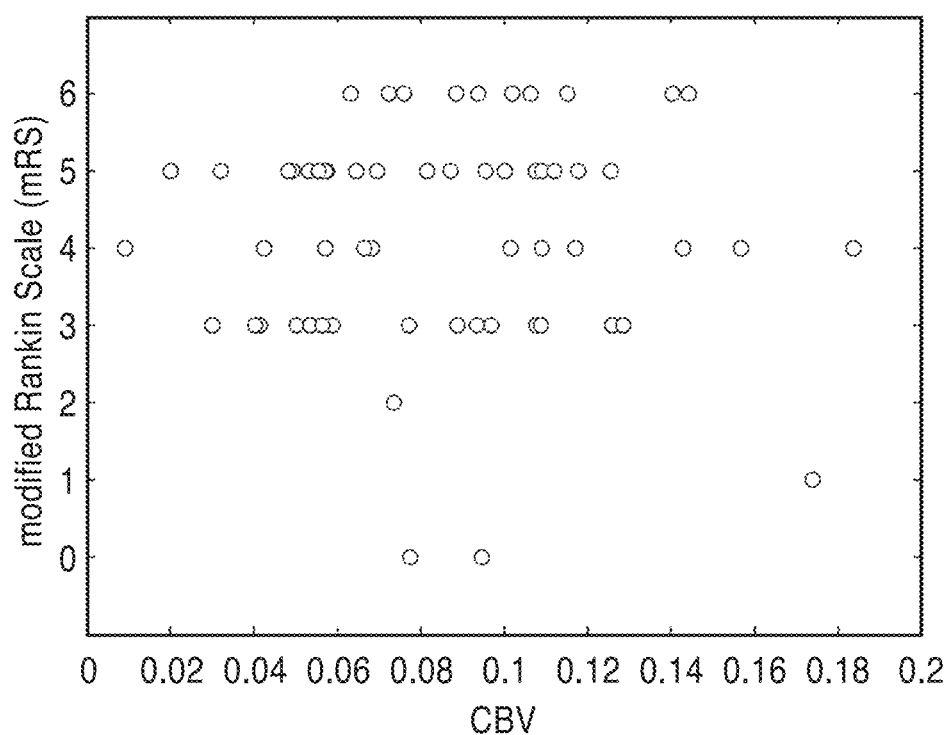
FIG. 6D is a scatter plot representing the perfusion angiography parameters CBV vs. mRS outcome.
Figure 6E:
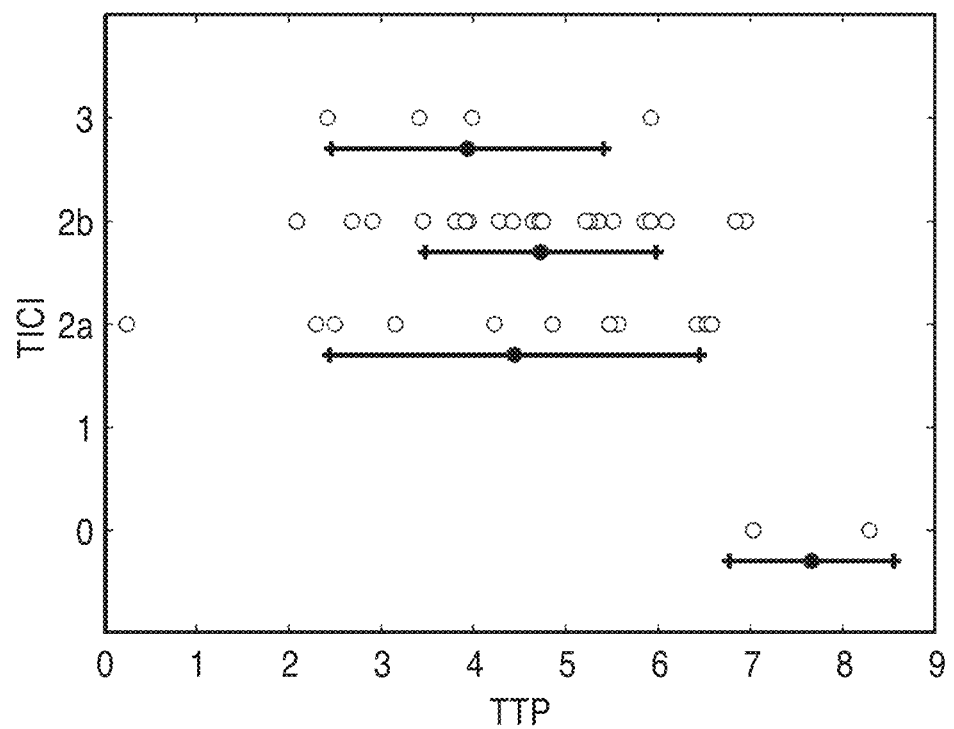
FIG. 6E is scatter plot representing the perfusion angiography parameter TTP versus TICI score. Average and standard deviation for specific TICI values are depicted by horizontal lines.
Figure 6F:
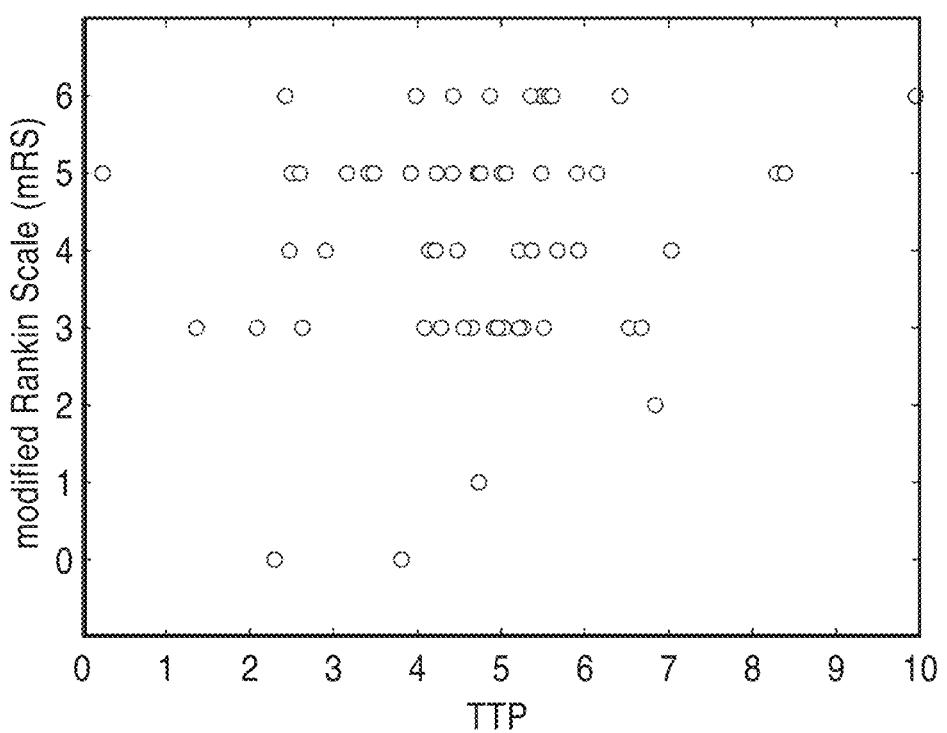
FIG. 6F is a scatter plot representing the perfusion angiography parameters TTP vs. mRS outcome.

Scatter plots representing the CBV and CBF perfusion angiography maps versus TICI score and MRS outcome are illustrated in FIG. 6A through FIG. 6F, where each patient is depicted as a circle. The plots include CBF vs. TICI (FIG. 6A), CBF vs. mRS (FIG. 6B), CBV vs. TICI (FIG. 6C), CBV vs. mRS (FIG. 6D), TTP vs. TICI (FIG. 6E), TTP vs. mRS (FIG. 6F).

When plotted versus TICI in FIG. 6A, CBF shows signs of a positive correlation (r=0:292; p<0:064). However, low CBF is not always synonymous with a poor TICI score as slower flow might still lead to a good revascularization and therefore a high TICI score. This may explain why larger TICI variations are observed for cases associated with low CBF. However, although the resolution of CBF is higher than TICI, it was not shown to be correlated with mRS (FIG. 6B). When CBV is studied with respect to TICI (FIG. 6C), it shows a weaker correlation (r=0:218; p<0:170).

The interpretation of the lack of correlation between CBV and mRS is different (FIG. 6D) as abnormal CBV may be represented by high or low values. It could be hypothesized that high mRS values are associated with larger variations in terms of CBV range; although this cannot be confirmed due to the biased distribution of the dataset.

Significantly higher delays in terms of TTP (FIG. 6E) were measured in the MCA territory for patients with no revascularization (TICI=0). For other TICI grades, there was no correlation with TTP. Similar to other maps, TTP was not correlated with mRS (FIG. 6F). The absence of equivalence between TICI and CBF/CBV estimated with perfusion angiography does not imply superiority of one measure to the other but rather it implies that they provide a different, perhaps complementary set of information.

Parametric maps were then computed for 8 patients. For each patient, the perfusion parameters were illustrated, including CBF, CBVfull (computed over the entire arteriovenous cycle), CBV (computed over the arterial phase), MTT, and TTP. Each parametric map is normalized and color-coded to facilitate visualization. Red was used to show high value (↑flow for CBF, ↑volume for CBV, and ↑delay for MTT and TTP), and blue was used to represent low values.

In addition, the source DSA on which perfusion angiography was performed is shown on the bottom row of each case. For matter of space, a subset of seven frames were sampled and displayed for each DSA sequence.

One of the aspects of the perfusion maps is that they are bidimensional. Therefore, a single image region may represent different anatomical structures that overlap across that region. Despite this limitation, these maps provide fine detail as they match the original spatial resolution of the DSA (1024×1024 in the dataset). The computation of the perfusion parameters for a single patient took 21 seconds. In principle, faster execution times can be obtained as the estimation of the perfusion parameters can be parallelized.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for quantitative analysis and visualization of blood flow parameters from digital subtraction angiography (DSA) images, the apparatus comprising: (a) an x-ray imager; (b) a computer processor; and (c) programming residing in a non-transitory computer readable medium, wherein the programming is executable by the computer processor and configured to: (i) acquire DSA image data of a subject from the imager; (ii) calculate concentration time curves of the arterial input function from the DSA images; (iii) extract perfusion parameters from the DSA images and concentration time curves; (iv) compute parametric maps of each extracted perfusion parameter data and DSA image data; and (v) display the parametric maps and DSA images on a visual display.

2. The apparatus of any preceding embodiment, further comprising color coding the parametric maps with a color indicating a perfusion parameter value is above or below a threshold value.

3. The apparatus of any preceding embodiment, wherein the concentration time curves of the arterial input function are calculated by averaging DSA concentration values within a region of interest at each time point.

4. The apparatus of any preceding embodiment, wherein the perfusion parameters extracted from the DSA images and concentration time curve data comprise Cerebral Blood Flow (CBF), Cerebral Blood Volume (CBV), Mean Transit Time (MTT), Time-to-Peak (TTP), and $T_{max}$.

5. The apparatus of any preceding embodiment, wherein the Cerebral Blood Volume (CBV) parameter extraction comprises: (a) measuring a total amount of contrast at a feeding arterial vessel ($C_a$); (b) calculating the amount of contrast agent ($C_u$) that has passed through a target location from DSA image intensities at the location; and (c) calculating Cerebral Blood Volume (CBV) with the relation:

$$CBV = \frac{\int_{t=0}^{\infty} C_u(t)dt}{\int_{t=0}^{\infty} C_a(t)dt}.$$

6. The apparatus of any preceding embodiment, wherein the Cerebral Blood Flow (CBF) parameter extraction comprises: (a) deconvoluting the tissue concentration ($C_u$) from arterial input ($C_a$) to produce a residue function R; and (b) deriving CBF as the maximum R value over time.

7. The apparatus of any preceding embodiment, wherein the Mean Transit Time (MTT) is calculated by dividing the Cerebral Blood Volume (CBF) by the Cerebral Blood Flow (CBF).

8. The apparatus of any preceding embodiment, further comprising: delineating individual contrast concentration curves of overlapping vessels with multivariate Gamma fitting.

9. A computer readable non-transitory medium comprising programming configured to be executed by at least one computer processor to perform quantitative analysis and visualization of blood flow parameters from digital subtraction angiography (DSA) images, comprising: (a) acquiring DSA image data of a subject from an x-ray imager; (b) calculating concentration time curves of the arterial input function from the DSA images; (c) extracting perfusion parameters from the DSA images and concentration time curves; (d) computing parametric maps of each extracted perfusion parameter data and DSA image data; (e) color coding the parametric maps with a color indicating a perfusion parameter value is within a range of values; and (f) displaying the parametric maps and DSA images on a visual display.

10. The programming of any preceding embodiment, wherein the concentration time curves of the arterial input function are calculated by averaging DSA concentration values within a region of interest at each time point.

11. The programming of any preceding embodiment, further comprising: delineating individual contrast concentration curves of overlapping vessels with multivariate Gamma fitting.

12. The programming of any preceding embodiment, wherein the perfusion parameters extracted from the DSA images and concentration time curve data comprise Cerebral Blood Flow (CBF), Cerebral Blood Volume (CBV), Mean Transit Time (MTT), Time-to-Peak (TTP), and $T_{max}$.

13. The programming of any preceding embodiment, wherein the Cerebral Blood Volume (CBV) parameter extraction comprises: (a) measuring a total amount of contrast at a feeding arterial vessel ($C_a$); (b) calculating the amount of contrast agent ($C_u$) that has passed through a target location from DSA image intensities at the location; and (c) calculating Cerebral Blood Volume (CBV) with the relation:

$$CBV = \frac{\int_{t=0}^{\infty} C_u(t)dt}{\int_{t=0}^{\infty} C_a(t)dt}.$$

14. The programming of any preceding embodiment, wherein the Cerebral Blood Flow (CBF) parameter extraction comprises: (a) deconvoluting the tissue concentration ($C_u$) from arterial input ($C_a$) to produce a residue function R; and (b) deriving CBF as the maximum R value over time.

15. The programming of any preceding embodiment, wherein the Mean Transit Time (MTT) is calculated by dividing the Cerebral Blood Volume (CBF) by the Cerebral Blood Flow (CBF).

16. A computer implemented method for the quantitative analysis and visualization of blood flow parameters from digital subtraction angiography (DSA) images, the method comprising: (a) acquiring DSA image data of a subject from an x-ray imager; (b) calculating concentration time curves of the arterial input function from the DSA images; (c) extracting perfusion parameters from the DSA images and concentration time curves; (d) computing parametric maps of each extracted perfusion parameter data and DSA image data; and (e) displaying the parametric maps and DSA images on a visual display.

17. The method of any preceding embodiment, further comprising: color coding the parametric maps with a color indicating a perfusion parameter value is within a range of values.

18. The method of any preceding embodiment, wherein the concentration time curves of the arterial input function are calculated by averaging DSA concentration values within a region of interest at each time point.

19. The method of any preceding embodiment, wherein the perfusion parameters extracted from the DSA images and concentration time curve data comprise Cerebral Blood Flow (CBF), Cerebral Blood Volume (CBV), Mean Transit Time (MTT), Time-to-Peak (TTP), and $T_{max}$.

20. The method of any preceding embodiment, wherein the Cerebral Blood Volume (CBV) parameter extraction comprises: (a) measuring a total amount of contrast at a feeding arterial vessel ($C_a$); (b) calculating the amount of contrast agent ($C_u$) that has passed through a target location from DSA image intensities at the location; and (c) calculating Cerebral Blood Volume (CBV) with the relation:

$$CBV = \frac{\int_{t=0}^{\infty} C_u(t)dt}{\int_{t=0}^{\infty} C_a(t)dt}.$$

21. The method of any preceding embodiment, wherein the Cerebral Blood Flow (CBF) parameter extraction comprises: (a) deconvoluting the tissue concentration ($C_u$) from arterial input ($C_a$) to produce a residue function R; and (b) deriving CBF as the maximum R value over time.

22. The method of any preceding embodiment, wherein the Mean Transit Time (MTT) is calculated by dividing the Cerebral Blood Volume (CBF) by the Cerebral Blood Flow (CBF).

23. The method of any preceding embodiment, further comprising: delineating individual contrast concentration curves of overlapping vessels with multivariate Gamma fitting.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for."

What is claimed is:
1. An apparatus for quantitative analysis and visualization of blood flow parameters from digital subtraction angiography (DSA) images, the apparatus comprising:
 (a) an x-ray imager;
 (b) a computer processor; and
 (c) programming residing in a non-transitory computer readable medium, wherein the programming is executable by the computer processor and configured to:

(i) acquire DSA images of a subject from the x-ray imager;
(ii) calculate concentration time curves of arterial input function from the DSA images;
(iii) extract perfusion parameters from the DSA images and concentration time curves;
(iv) compute parametric maps of each extracted perfusion parameter data and DSA image data; and
(v) display the parametric maps and DSA images on a visual display;
(d) wherein said perfusion parameters extracted from the DSA images and concentration time curves by said programming comprise Cerebral Blood Flow (CBF), Cerebral Blood Volume (CBV), Mean Transit Time (MTT), Time-to-Peak (TTP), and $T_{max}$; and
(e) wherein extraction of the Cerebral Blood Volume (CBV) perfusion parameter by said programming comprises:
(i) measuring a total amount of contrast at a feeding arterial vessel (Ca);
(ii) calculating the amount of contrast agent (Cu) that has passed through a target location from DSA image intensities at the location; and
(iii) calculating Cerebral Blood Volume (CBV) with the relation:

$$CBV = \frac{\int_{t=0}^{\infty} C_u(t)dt}{\int_{t=0}^{\infty} C_a(t)dt}.$$

2. The apparatus of claim 1, further comprising color coding the parametric maps with a color indicating a perfusion parameter value is above or below a threshold value.

3. The apparatus of claim 1, wherein said concentration time curves of the arterial input function are calculated by averaging DSA concentration values within a region of interest at each time point.

4. The apparatus of claim 1, wherein the Cerebral Blood Flow (CBF) parameter extraction comprises:
(a) deconvoluting the tissue concentration (Cu) from arterial input (Ca) to produce a residue function R; and
(b) deriving CBF as the maximum R value over time.

5. The apparatus of claim 1, wherein the Mean Transit Time (MTT) is calculated by dividing the Cerebral Blood Volume (CBF) by the Cerebral Blood Flow (CBF).

6. The apparatus of claim 1, further comprising: delineating individual contrast concentration curves of overlapping vessels with multivariate Gamma fitting.

7. A computer readable non-transitory medium comprising programming configured to be executed by at least one computer processor to perform quantitative analysis and visualization of blood flow parameters from digital subtraction angiography (DSA) images, comprising:
(a) acquiring DSA images of a subject from an x-ray imager;
(b) calculating concentration time curves of arterial input function from the DSA images;
(c) extracting perfusion parameters from the DSA images and concentration time curves;
(d) computing parametric maps of each extracted perfusion parameter data and DSA image data;
(e) color coding the parametric maps with a color indicating a perfusion parameter value is within a range of values; and (f) displaying the parametric maps and DSA images on a visual display;
(g) wherein said perfusion parameters extracted from the DSA images and concentration time curve data comprise Cerebral Blood Flow (CBF), Cerebral Blood Volume (CBV), Mean Transit Time (MTT), Time-to-Peak (TTP), and $T_{max}$; and
(h) wherein the Cerebral Blood Volume (CBV) parameter extraction comprises:
(i) measuring a total amount of contrast at a feeding arterial vessel (Ca);
(ii) calculating the amount of contrast agent (Cu) that has passed through a target location from DSA image intensities at the location; and
(iii) calculating Cerebral Blood Volume (CBV) with the relation:

$$CBV = \frac{\int_{t=0}^{\infty} C_u(t)dt}{\int_{t=0}^{\infty} C_a(t)dt}.$$

8. The computer readable non-transitory medium of claim 7, wherein said concentration time curves of the arterial input function are calculated by averaging DSA concentration values within a region of interest at each time point.

9. The computer readable non-transitory medium claim 7, wherein said programming further performs steps comprising: delineating individual contrast concentration curves of overlapping vessels with multivariate Gamma fitting.

10. The computer readable non-transitory medium of claim 7, wherein the Cerebral Blood Flow (CBF) parameter extraction comprises:
(a) deconvoluting the tissue concentration (Cu) from arterial input (Ca) to produce a residue function R; and
(b) deriving CBF as the maximum R value over time.

11. The computer readable non-transitory medium of claim 7, wherein the Mean Transit Time (MTT) is calculated by dividing the Cerebral Blood Volume (CBF) by the Cerebral Blood Flow (CBF).

12. A computer implemented method for the quantitative analysis and visualization of blood flow parameters from digital subtraction angiography (DSA) images, the method comprising:
(a) acquiring DSA images of a subject from an x-ray imager;
(b) calculating concentration time curves of arterial input function from the DSA images;
(c) extracting perfusion parameters from the DSA images and concentration time curves;
(d) computing parametric maps of each extracted perfusion parameter data and DSA image data; and
(e) displaying the parametric maps and DSA images on a visual display;
(f) wherein said perfusion parameters extracted from the DSA images and concentration time curve data comprise Cerebral Blood Flow (CBF), Cerebral Blood Volume (CBV), Mean Transit Time (MTT), Time-to-Peak (TTP), and $T_{max}$; and
(g) wherein the Cerebral Blood Volume (CBV) parameter extraction comprises:
(i) measuring a total amount of contrast at a feeding arterial vessel (Ca);
(ii) calculating the amount of contrast agent (Cu) that has passed through a target location from DSA image intensities at the location; and (iii) calculating Cerebral Blood Volume (CBV) with the relation:

$$CBV = \frac{\int_{t=0}^{\infty} C_u(t)dt}{\int_{t=0}^{\infty} C_a(t)dt}.$$

13. The method of claim 12, further comprising:
    color coding the parametric maps with a color indicating a perfusion parameter value is within a range of values.

14. The method of claim 12, wherein said concentration time curves of the arterial input function are calculated by averaging DSA concentration values within a region of interest at each time point.

15. The method of claim 12, wherein the Cerebral Blood Flow (CBF) parameter extraction comprises:
    (a) deconvoluting the tissue concentration (Cu) from arterial input (Ca) to produce a residue function R; and
    (b) deriving CBF as the maximum R value over time.

16. The method of claim 12, wherein the Mean Transit Time (MTT) is calculated by dividing the Cerebral Blood Volume (CBF) by the Cerebral Blood Flow (CBF).

17. The method of claim 12, further comprising: delineating individual contrast concentration curves of overlapping vessels with multivariate Gamma fitting.

\* \* \* \* \*